(12) United States Patent
Tanaka

(10) Patent No.: US 10,398,403 B2
(45) Date of Patent: Sep. 3, 2019

(54) HIGH VOLTAGE GENERATION APPARATUS, X-RAY CT APPARATUS, AND POWER SUPPLY APPARATUS

(71) Applicant: Toshiba Medical Systems Corporation, Otawara-shi (JP)

(72) Inventor: Kimio Tanaka, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 361 days.

(21) Appl. No.: 15/339,152

(22) Filed: Oct. 31, 2016

(65) Prior Publication Data

US 2017/0209114 A1    Jul. 27, 2017

(30) Foreign Application Priority Data

Jan. 25, 2016    (JP) .................................. 2016-011864

(51) Int. Cl.
| | |
|---|---|
| *A61B 6/00* | (2006.01) |
| *A61B 6/03* | (2006.01) |
| *H05G 1/10* | (2006.01) |
| *A61B 6/06* | (2006.01) |

(52) U.S. Cl.
CPC ............... *A61B 6/56* (2013.01); *A61B 6/032* (2013.01); *A61B 6/405* (2013.01); *A61B 6/542* (2013.01); *H05G 1/10* (2013.01); *A61B 6/06* (2013.01); *A61B 6/465* (2013.01)

(58) Field of Classification Search
None
See application file for complete search history.

(56) References Cited

U.S. PATENT DOCUMENTS

| | | | |
|---|---|---|---|
| 4,596,029 A | | 6/1986 | Manueco Santurtun et al. |
| 5,034,973 A | * | 7/1991 | Ishiyama ............ H05G 1/10 363/16 |

FOREIGN PATENT DOCUMENTS

| | | |
|---|---|---|
| JP | 60-221997 | 11/1985 |
| JP | 2013-140739 | 7/2013 |

\* cited by examiner

*Primary Examiner* — Hoon K Song
(74) *Attorney, Agent, or Firm* — Oblon, McClelland, Maier & Neustadt, L.L.P.

(57) ABSTRACT

A high voltage generation apparatus according to an embodiment includes power factor improvement circuitry and gain adjustment circuitry. The power factor improvement circuitry improves a power factor of alternating current (AC) power output from an AC power source in order to supply an X-ray tube with power that is controlled based on a reference voltage. The gain adjustment circuitry is included in the power factor improvement circuitry, and adjusts a gain of an output voltage relative to the reference voltage so that the gain differs between a first period including a start of irradiation of X-rays by the X-ray tube or an end of irradiation of X-rays by the X-ray tube, and a second period different from the first period.

20 Claims, 11 Drawing Sheets

HIGH VOLTAGE GENERATION APPARATUS, X-RAY CT APPARATUS, AND POWER SUPPLY APPARATUS

CROSS-REFERENCE TO RELATED APPLICATIONS

This application is based upon and claims the benefit of priority from Japanese Patent Application No. 2016-011864, filed on Jan. 25, 2016; the entire contents of which are incorporated herein by reference.

FIELD

Embodiments described herein relate generally to a high voltage generation apparatus, an X-ray computed tomography (CT) apparatus, and a power supply apparatus.

BACKGROUND

A high voltage generation apparatus supplies a tube voltage to an X-ray tube included in an X-ray CT apparatus. The high voltage generation apparatus needs to improve a power factor in order to meet harmonic regulations. Examples of a method of improving the power factor of the high voltage generation apparatus include a method using a reactor and a method using power factor improvement circuitry (power factor corrector (PFC)).

The use of a reactor improves the power factor of the high voltage generation apparatus to be approximately 0.8. In this case, a reactor compatible with 50 Hz or 60 Hz is used. The power factor obtained by the use of the reactor, however, is smaller than a power factor obtained by the use of power factor improvement circuitry. Furthermore, the reactor compatible with 50 Hz or 60 Hz is large in dimensions and weight. The dimensions and weight of the high voltage generation apparatus are accordingly increased.

The use of power factor improvement circuitry improves the power factor of the high voltage generation apparatus to be approximately 0.95 to approximately 0.99. This enables apparent power of an alternating current (AC) power source configured to supply power to ar X-ray tube to be reduced to suppress the capacity of the AC power source while suppressing the increase in dimensions and weight of the high voltage generation apparatus. When the irradiation of X-rays is started, however, a load applied to the high voltage generation apparatus abruptly increases, and an output voltage of the power factor improvement circuitry decreases. When the irradiation of X-rays is ended, the load applied to the high voltage generation apparatus abruptly decreases, and the output voltage of the power factor improvement circuitry increases. Thus, for example, a tube voltage may fluctuate so that the dose of the X-rays radiated from the X-ray tube may fluctuate.

DETAILED DESCRIPTION

A high voltage generation apparatus according to embodiments described herein includes power factor improvement circuitry and gain adjustment circuitry. The power factor improvement circuitry improves a power factor of AC power output from an AC power source in order to supply an X-ray tube with power that is controlled based or a reference voltage. The gain adjustment circuitry is included in the power factor improvement circuitry, and adjusts a gain of an output voltage relative to the reference voltage so that the gain differs between a first period including a start of irradiation of X-rays by the X-ray tube or an end of irradiation of X-rays by the X-ray tube, and a second period different from the first period.

Referring to the accompanying drawings, a high voltage generation apparatus, an X-ray CT apparatus, and power supply apparatus according to the embodiments are now described. Note that, in the following embodiments, overlapping descriptions are omitted as appropriate.

First Embodiment

Figure 1:
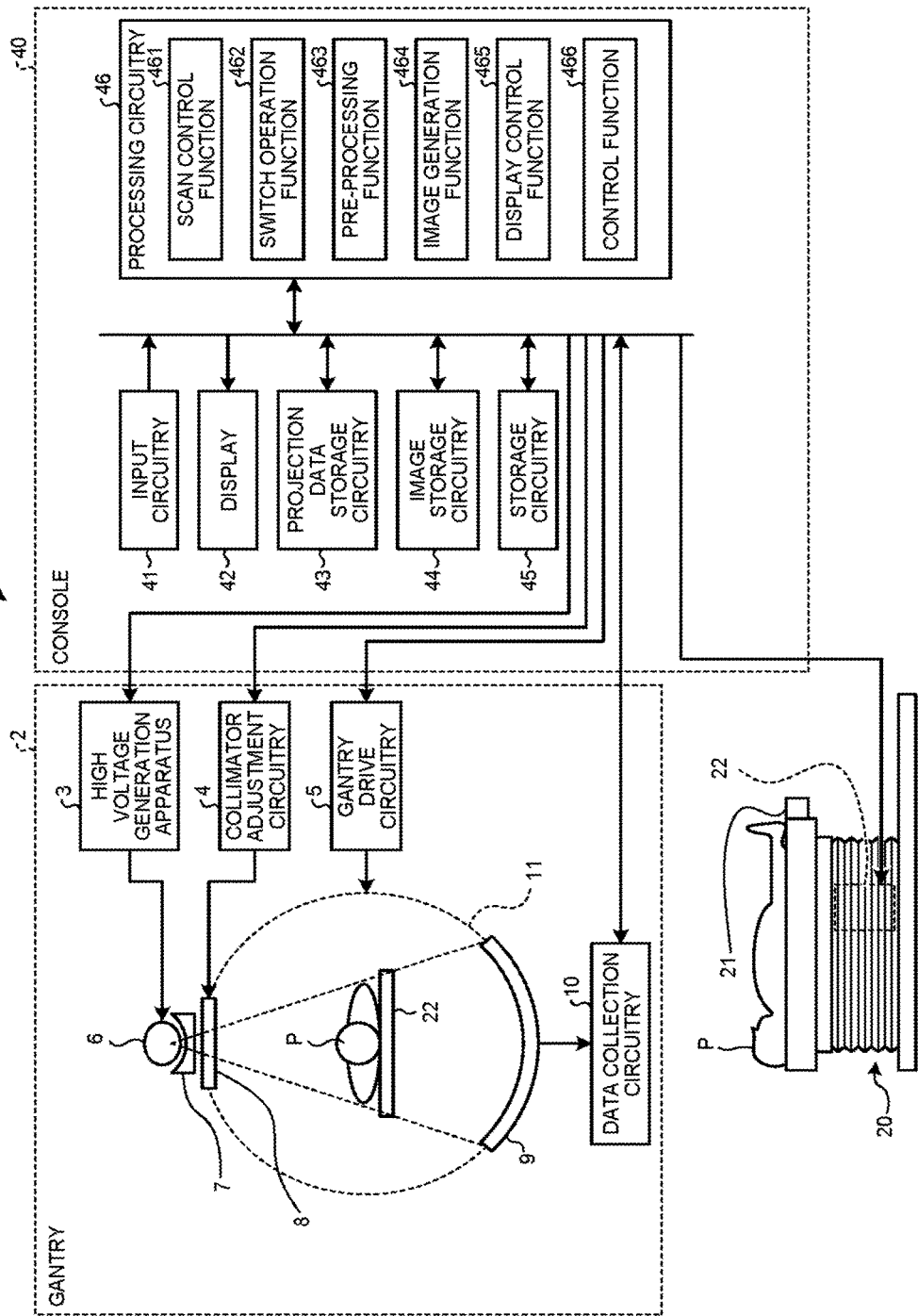
FIG. 1 is a diagram illustrating a configuration example of an X-ray CT apparatus according to a first embodiment.

Referring to FIG. 1, the configuration of an X-ray CT apparatus 1 according to a first embodiment is now described. FIG. 1 is a diagram illustrating a configuration example of the X-ray CT apparatus according to the first embodiment. As illustrated in FIG. 1, the X-ray CT apparatus 1 includes a gantry 2, a couch 20, and a console 40. Note that the configuration of the X-ray CT apparatus 1 is not limited to the following configuration.

The gantry 2 includes a high voltage generation apparatus 3, collimator adjustment circuitry 4, gantry drive circuitry 5, an X-ray tube 6, a wedge 7, a collimator 8, a detector 9, data collection circuitry 10, and a rotating frame 11.

The high voltage generation apparatus 3 supplies a tube voltage to the X-ray tube 6. Details of the high voltage generation apparatus 3 are described later.

The collimator adjustment circuitry 4 adjusts the aperture and position of the collimator 8 to adjust an irradiation range of X-rays generated by the X-ray tube 6. The gantry drive circuitry 5 rotates the rotating frame 11 to turn the X-ray tube 6 and the detector 9 on a circular orbit around a subject P. The X-ray tube 6 generates X-rays with the tube voltage supplied from the high voltage generation apparatus 3. The wedge 7 is an X-ray filter for adjusting the dose of the X-rays generated by the X-ray tube 6. The collimator 8 is a slit for adjusting the irradiation range of the X-rays. The aperture and position of the collimator 8 are adjusted by the collimator adjustment circuitry 4.

The detector 9 detects X-rays. The detector 9 includes a plurality of detection elements. The detector 9 detects the X-rays generated by the X-ray tube 6 with the detection elements. The detection elements convert the incident X-rays into an electric signal and output the converted electric signal to the data collection circuitry 10. The size, shape, and number of the detection elements included in the detector 9 are not particularly limited. Note that the detector 9 may be either of a direct conversion detector or an indirect conversion detector. The data collection circuitry 10 generates projection data based on the electric signal output from the detection elements. The rotating frame 11 is an annular frame. The rotating frame 11 supports the X-ray tube 6 and the detector 9. The X-ray tube 6 and the detector 9 are facing each other. The rotating frame 11 is driven by the gantry drive circuitry 5 to rotate about the subject P.

The couch 20 includes a couchtop 21 and couch drive circuitry 22. The couchtop 21 is a plate-shaped member for putting the subject P thereon. The couch drive circuitry 22 moves the couchtop 21 having the subject P put thereon, thereby moving the subject P within an imaging space in the gantry 2.

The console 40 includes input circuitry 41, a display 42, projection data storage circuitry 43, image storage circuitry 44, storage circuitry 45, and processing circuitry 46.

The input circuitry 41 is used by a user to input instructions and settings. For example, the input circuitry 41 is included in a mouse or a keyboard. The input circuitry 41 transfers the instructions and settings input by the user to the processing circuitry 46. For example, the input circuitry 41 is implemented by a processor.

The display 42 is a monitor to be referred to by the user. For example, the display 42 receives, from the processing circuitry 46, an instruction to display a CT image or a graphical user interface (GUI) used for the user to input instructions and settings. The display 42 displays a CT image or a GUI based on the instruction.

The projection data storage circuitry 43 stores therein raw data generated by a pre-processing function 463 described later. The image storage circuitry 44 stores therein CT images generated by an image generation function 464 described later.

The storage circuitry 45 stores therein a computer program used for the high voltage generation apparatus 3, the collimator adjustment circuitry 4, the gantry drive circuitry 5, and the data collection circuitry 10 to implement the above-mentioned function. The storage circuitry 45 stores therein a computer program used for the couch drive circuitry 22 to implement the above-mentioned function. The storage circuitry 45 stores therein a computer program used for the processing circuitry 46 to implement each of a scan control function 461, a switch operation function 462, the pre-processing function 463, the image generation function 464, a display control function 465, a control function 466, and other functions described later. Therefore, the high voltage generation apparatus 3, the collimator adjustment circuitry 4, the gantry drive circuitry 5, the data collection circuitry 10, the couch drive circuitry 22, and the processing circuitry 46 implement their functions by reading and executing the computer programs stored in the storage circuitry 45.

Furthermore, the projection data storage circuitry 43, the image storage circuitry 44, and the storage circuitry 45 each include a storage medium whose stored information is readable by a computer. Examples of the storage medium include a hard disk.

The processing circuitry 46 has the scan control function 461, the switch operation function 462, the pre-processing function 463, the image generation function 464, the display control function 465, and the control function 466. Details of these functions are described later. For example, the processing circuitry 46 is implemented by a processor.

Figure 2:
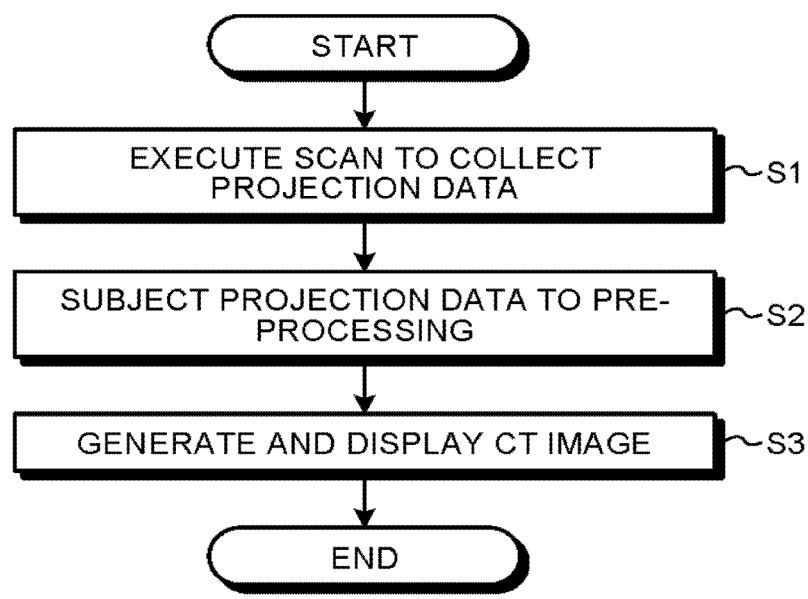
FIG. 2 is a flowchart illustrating an example of processing performed by the X-ray CT apparatus according to the first embodiment.

Referring to FIG. 2, an example of processing of the X-ray CT apparatus 1 according to the first embodiment is now described. FIG. 2 is a flowchart illustrating an example of processing performed by the X-ray CT apparatus according to the first embodiment.

As illustrated in FIG. 2, the processing circuitry 46 execute a scan to collect projection data (Step S1). For example, the processing of Step S1 is as follows.

The processing circuitry 46 reads a computer program corresponding to the scan control function 461 from the storage circuitry 45, and executes the read computer program. The scan control function 461 is a function of controlling the X-ray CT apparatus 1 in order to execute a scan. For example, the processing circuitry 46 executes the scan control function 461 to control the X-ray CT apparatus 1 as follows.

The processing circuitry 46 controls the couch drive circuitry 22 to move the subject P into an imaging space in the gantry 2. The processing circuitry 46 controls the gantry 2 to scan the subject P. Specifically, the processing circuitry 46 controls the high voltage generation apparatus 3 to supply a tube voltage to the X-ray tube 6. The processing circuitry 46 controls the collimator adjustment circuitry 4 to adjust the aperture and position of the collimator 8. Furthermore, the processing circuitry 46 controls the gantry drive circuitry 5 to rotate the rotating frame 11. Then, the processing circuitry 46 controls the data collection circuitry 10 so that the data collection circuitry 10 collects projection data. Examples of the scan executed by the X-ray CT apparatus 1 include conventional scan, helical scan, and step-and-shoot scan.

Furthermore, the processing circuitry 46 reads a computer program corresponding to the switch operation function 462 from the storage circuitry 45, and executes the read computer program. Details of the switch operation function 462 are described later.

As illustrated in FIG. 2, the processing circuitry 46 subjects the projection data to pre-processing (Step S2). For example, the processing of Step S2 is as follows.

The processing circuitry 46 reads a computer program corresponding to the pre-processing function 463 from the storage circuitry 45, and executes the read computer program. The pre-processing function 463 is a function of correcting the projection data generated by the data collection circuitry 10. Examples of the correction include logarithmic transformation, offset correction, sensitivity correction, beam hardening correction, and scattering radiation correction. The projection data corrected by the pre-processing function 463 is stored in the projection data storage circuitry 43. Note that the projection data corrected by the pre-processing function 463 is referred to also as "raw data".

As illustrated in FIG. 2, the processing circuitry 46 generates and displays a CT image (Step S3). For example, the processing of Step S3 is as follows.

The processing circuitry 46 reads a computer program corresponding to the image generation function 464 from the storage circuitry 45, and executes the read computer program. The image generation function 464 is a function of reconstructing the raw data stored in the projection data storage circuitry 43 to generate a CT image. Examples of the reconstruction method include back projection and iterative reconstruction. The processing circuitry 46 reads a computer program corresponding to the display control function 465 from the storage circuitry 45, and executes the read computer program. The display control function 465 is a function of displaying the CT image stored in the image storage circuitry 44 on the display 42.

Note that the processing circuitry 46 reads a computer program corresponding to the control function 466 from the storage circuitry 45 and executes the read computer program as appropriate in order to execute the above-mentioned processing. The control function 466 includes a function of operating each component of the gantry 2, the couch 26, and the console 40 at timing suited for the purpose, and other functions.

Figure 3:
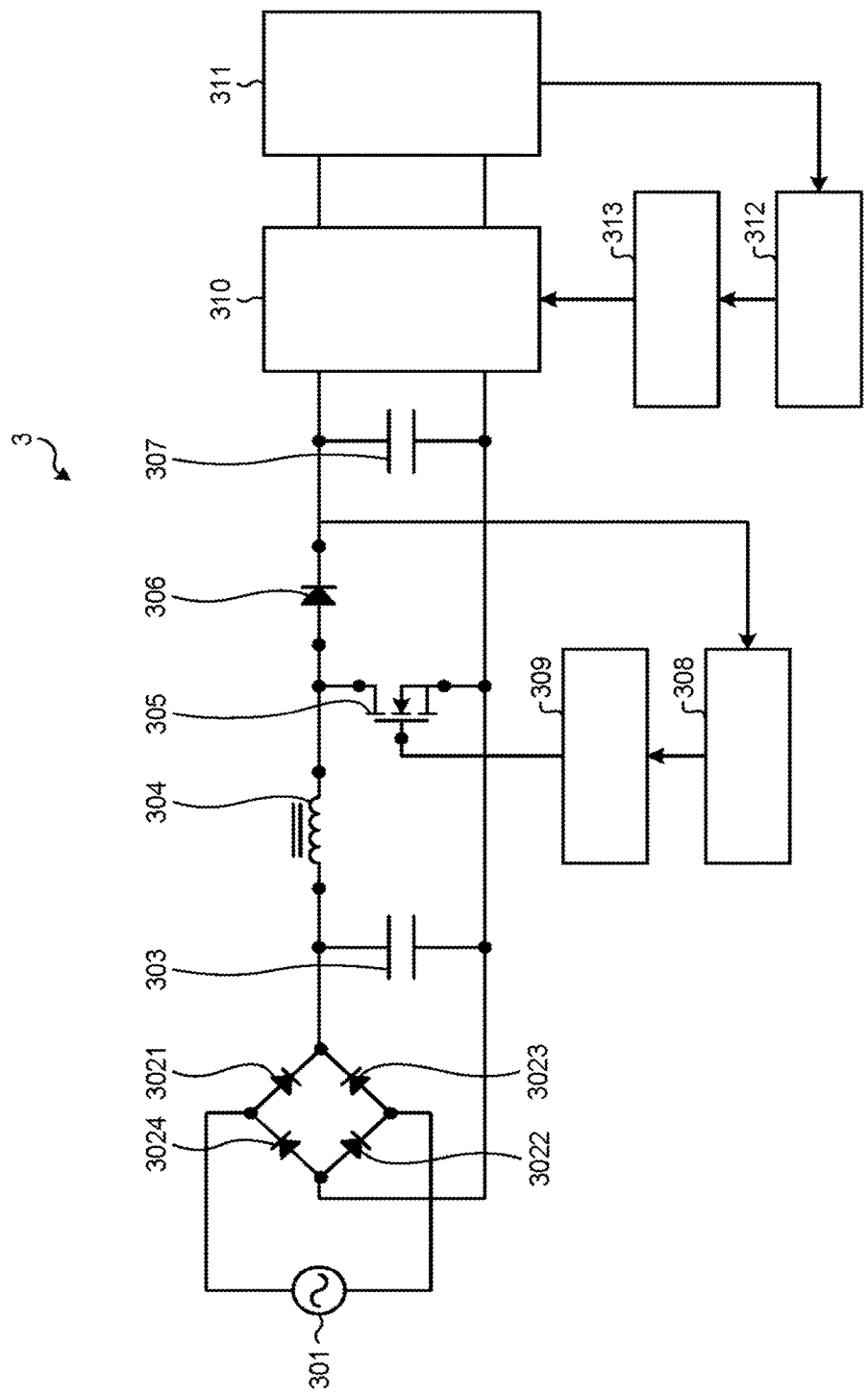
FIG. 3 is a diagram illustrating a configuration example of a high voltage generation apparatus according to the first embodiment.
Figure 4:
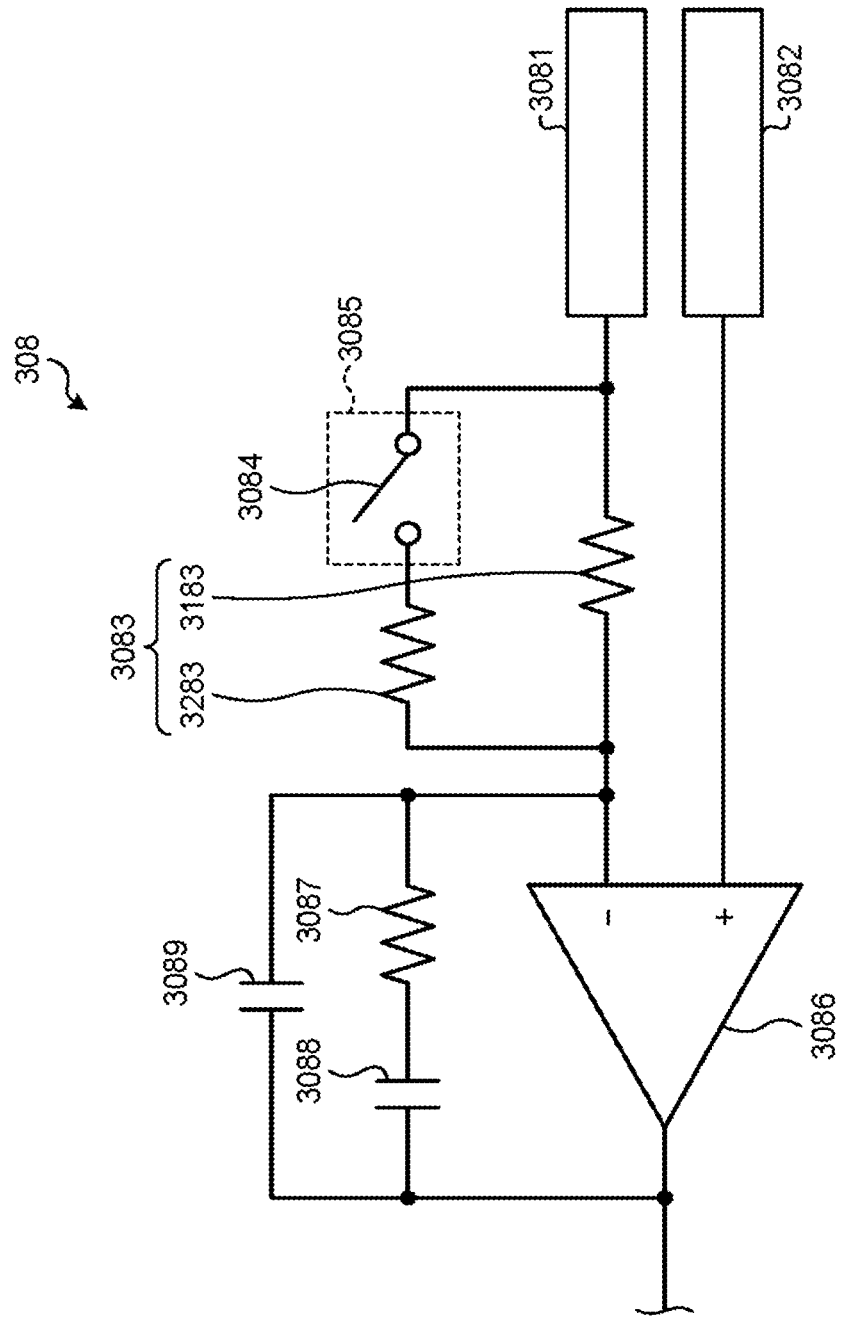
FIG. 4 is a diagram illustrating a configuration example of feedback circuitry according to the first embodiment.

Referring to FIG. 3 and FIG. 4, the configuration of the high voltage generation apparatus 3 according to the first embodiment is now described. FIG. 3 is a diagram illustrating a configuration example of the high voltage generation apparatus according to the first embodiment. FIG. 4 is a diagram illustrating a configuration example of feedback circuitry according to the first embodiment.

As illustrated in FIG. 3, the high voltage generation apparatus 3 includes an AC power source 301, a diode 3021, a diode 3022, a diode 3023, a diode 3024, a capacitor 303, a coil 304, an n-type metal-oxide semiconductor field-effect transistor (MOSFET) 305, a diode 306, a capacitor 307, feedback circuitry 308, switching circuitry 309, inverter circuitry 310, high voltage generation circuitry 311, feedback circuitry 312, and switching circuitry 313.

One terminal of the AC power source 301 is connected to an anode of the diode 3021 and a cathode of the diode 3024. The other terminal of the AC power source 301 is connected to a cathode of the diode 3022 and an anode of the diode 3023.

The diode 3021, the diode 3022, the diode 3023, and the diode 3024 form a diode bridge. Accordingly, the four diodes are connected as follows.

The anode of the diode 3021 is connected to the one terminal of the AC power source 301 and the cathode of the diode 3024. A cathode of the diode 3021 is connected to cathode of the diode 3023 and one terminal of the capacitor 303. An anode of the diode 3022 is connected to an anode of the diode 3024 and the other terminal of the capacitor 303. The cathode of the diode 3022 is connected to the other terminal of the AC power source 301 and the anode of the diode 3023.

The anode of the diode 3023 is connected to the other terminal of the AC power source 301 and the cathode of the diode 3022. The cathode of the diode 3023 is connected the cathode of the diode 3021 and the one terminal of the capacitor 303. The anode of the diode 3024 is connected to the anode of the diode 3022 and the other terminal of the capacitor 303. The cathode of the diode 3024 is connected to the one terminal of the AC power source 301 and the anode of the diode 3021.

The one terminal of the capacitor 303 is connected to the cathode of the diode 3021, the cathode of the diode 3023, and one terminal of the coil 304. The other terminal of the capacitor 303 is connected to the anode of the diode 3022, the anode of the diode 3024, and a source electrode of the n-type MOSFET 305.

The coil 304, the n-type MOSFET 305, the diode 306, and the capacitor 307 form booster circuitry. Accordingly, these components are connected as follows.

The one terminal of the coil 304 is connected to the cathode of the diode 3021, the cathode of the diode 3023, and the one terminal of the capacitor 303. The other terminal of the coil 304 is connected to a drain electrode of the n-type MOSFET 305 and an anode of the diode 306.

A gate electrode of the n-type MOSFET 305 is connected to an output terminal of the switching circuitry 309, The drain electrode of the n-type MOSFET 305 is connected to the other terminal of the coil 304 and the anode of the diode 306 The source electrode of the n-type MOSFET 305 is connected to the anode of the diode 3022, the anode of the diode 3024, the other terminal of the capacitor 303, and the other terminal of the capacitor 307.

The anode of the diode 306 is connected to the other terminal of the coil 304 and the drain electrode of the n-type MOSFET 305. A cathode of the diode 306 is connected to one terminal of the capacitor 307 and an input terminal of the feedback circuitry 308.

The one terminal of the capacitor 307 is connected to the cathode of the diode 306, the input terminal of the feedback circuitry 308, and the inverter circuitry 310. The other terminal of the capacitor 307 is connected to the anode of the diode 3022, the anode of the diode 3024, the other terminal of the capacitor 303, the source electrode of the n-type MOSFET 305, and the inverter circuitry 310. The capacitor 307 has capacitance of 1,000 µF, for example.

As illustrated in FIG. 4, the feedback circuitry 308 includes a first input terminal 3081, a second input terminal 3082, a first resistor 3083, a switch 3084, a switch operation mechanism 3085, an operational amplifier 3086, a second resistor 3087, a capacitor 3088, and a capacitor 3089.

The first input terminal 3081 supplies a voltage generated between two terminals of the capacitor 307 to an inverting input terminal of the operational amplifier 3086. One terminal of the first input terminal 3081 is connected to the cathode of the diode 306 and the one terminal of the capacitor 337. The other terminal of the first input terminal 3081 is connected to one terminal of a resistor 3183 and one terminal of the switch 3084.

The second input terminal 3082 supplies a reference voltage to a non-inverting input terminal of the operational amplifier 3086. One terminal of the second input terminal 3052 is connected to, for example, circuitry configured to supply the reference voltage to the operational amplifier 3086. The other terminal of the second input terminal 3082 is connected to the non-inverting input terminal of the operational amplifier 3086.

The first resistor 3083 includes the resistor 3183 and a resistor 3283. A voltage output from power factor improvement circuitry is input to the first resistor 3083. Specifically, the voltage generated between two terminals of the capacitor 307 is input to the first resistor 3083. The one terminal f the resistor 3183 is connected to the other terminal of the first input terminal 3081 and the one terminal of the switch 3084. The other terminal of the resistor 3133 is connected to the other terminal of the resistor 3283, the inverting input terminal of the operational amplifier 3086, one terminal of the second resistor 3087, and one terminal of the capacitor 3089.

The switch 3084 changes a resistance value of the first resistor 3083. Specifically, the switch 3084 discretely changes the resistance value of the first resistor 3083. For example, the switch 3084 discretely changes the resistance value of the first resistor 3083 by switching a resistor that contributes to the resistance value of the first resistor 3083. For another example, the switch 3084 continuously changes the resistance value of the first resistor 3083. The configuration of the switch 3084 is not particularly limited. The one terminal of the switch 3084 is connected to the other terminal of the first input terminal 3081 and the one terminal of the resistor 3183. The other terminal of the switch 3084 is connected to one terminal of the resistor 3283.

The one terminal of the resistor 3283 is connected to the other terminal of the switch 3084. The other terminal of the resistor 3283 is connected to the other terminal of the resistor 3183, the inverting input terminal of the operational amplifier 3086, the one terminal of the second resistor 3087, and the one terminal of the capacitor 3089.

Gain adjustment circuitry switches the switch 3084 to change the resistance value of the first resistor, thereby increasing a gain for a first period. The gain adjustment circuitry is, for example, the switch operation mechanise 3085. The configuration of the switch operation mechanism 3085 is not particularly limited. The switch operation mechanism 3085 only needs to switch ON and OFF of the switch 3084.

The non-inverting input terminal of the operational amplifier 3086 is connected to the other terminal of the second input terminal 3082. The inverting input terminal of the operational amplifier 3086 is connected to the other terminal of the resistor 3183, the other terminal of the resistor 3283, the one terminal of the second resistor 3087, and the one terminal of the capacitor 3089. An output terminal of the operational amplifier 3086 is connected to the other terminal of the capacitor 3088, the other terminal of the capacitor 3089, and an input terminal of the switching circuitry 309.

The one terminal of the second resistor 3087 is connected to the other terminal of the resistor 3183, the other terminal of the resistor 3283, the inverting input terminal of the operational amplifier 3086, and the one terminal of the capacitor 3089. The other terminal of the second resistor 3087 is connected to one terminal of the capacitor 3088. In other words, the other terminal of the second resistor 3087 is connected to the output terminal of the operational amplifier 3086 via the capacitor 3088.

The one terminal of the capacitor 3089 is connected to the other terminal of the second resistor 3097. In other words, the one terminal of the capacitor 3088 is connected to the inverting input terminal of the operational amplifier 3086 via the second resistor 3087. The other terminal of the capacitor 3008 is connected to the output terminal of the operational amplifier 3086, the other terminal of the capacitor 3089, and the input terminal of the switching circuitry 309.

The one terminal of the capacitor 3089 is connected to the other terminal of the resistor 3183, the other terminal of the resistor 3283, the inverting input terminal of the operational amplifier 3086, and the one terminal of the second resistor 3087. The other terminal of the capacitor 3089 is connected to the output terminal of the operational amplifier 3086, the other terminal of the capacitor 3086, and the input terminal of the switching circuitry 309.

As illustrated in FIG. 3, the input terminal of the switching circuitry 309 is connected to an output terminal of the feedback circuitry 308. The output terminal of the switching circuitry 309 is connected to the gate electrode of the n-type MOSFET 305.

Note that the diode 3021, the diode 3022, the diode 3023, the diode 3024, the capacitor 303, the coil 304, the n-type MOSFET 305, the diode 306, the capacitor 307, the feedback circuitry 308, and the switching circuitry 309 form the power factor improvement circuitry. The power factor improvement circuitry improves a power factor of AC power output from the AC power source 301 in order to supply the X-ray tube 6 with power that is controlled based on the reference voltage.

The inverter circuitry 310 includes switching elements. Examples of the switching elements include a MOSFET and an insulated gate bipolar transistor (IGBT). The inverter circuitry 310 is connected to two terminals of the capacitor 307 and the high voltage generation circuitry 311. Furthermore, the switching elements included in the inverter circuitry 310 are connected to an output terminal of the switching circuitry 313.

The high voltage generation circuitry 311 is connected to the inverter circuitry 310, an input terminal of the feedback circuitry 312, and the X-ray tube 6.

The configuration of the feedback circuitry 312 is the same as, for example, circuitry obtained by replacing the first resistor 3083, the switch 3084, and the switch operation mechanism 3085 included in the feedback circuitry 308 with resistors. A first input terminal of the feedback circuitry 312 is connected to the high voltage generation circuitry 311. A second input terminal of the feedback circuitry 312 is connected to, for example, the circuitry configured to supply the reference voltage. An output terminal of the feedback circuitry 312 is connected to an input terminal of the switching circuitry 313.

The configuration of the switching circuitry 313 is the same as, for example, the configuration of the switching circuitry 309. The input terminal of the switching circuitry 313 is connected to the output terminal of the feedback circuitry 312. The output terminal of the switching circuitry 313 is connected to the switching elements included in the inverter circuitry 310.

Figure 5:
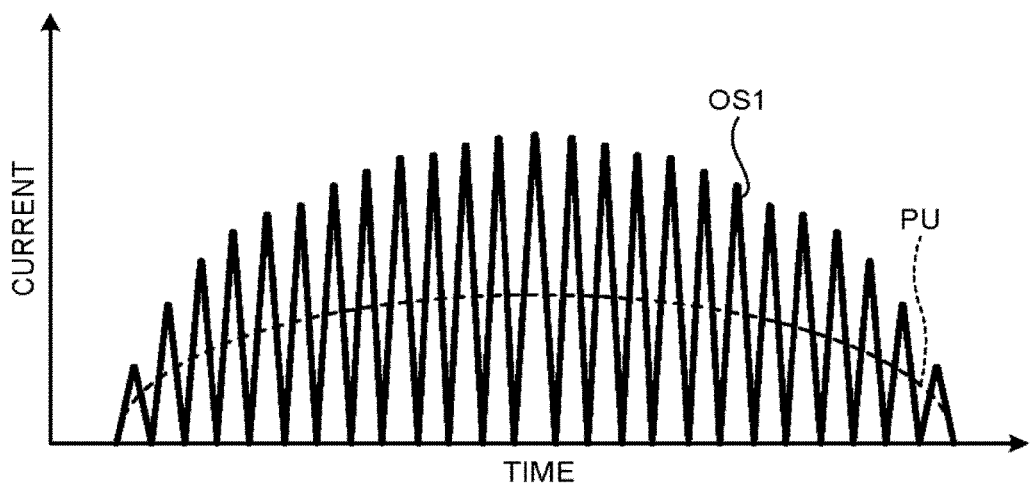
FIG. 5 is a graph illustrating an example of an oscillating component contained in a pulsating current generated by full-wave rectification.
Figure 6:
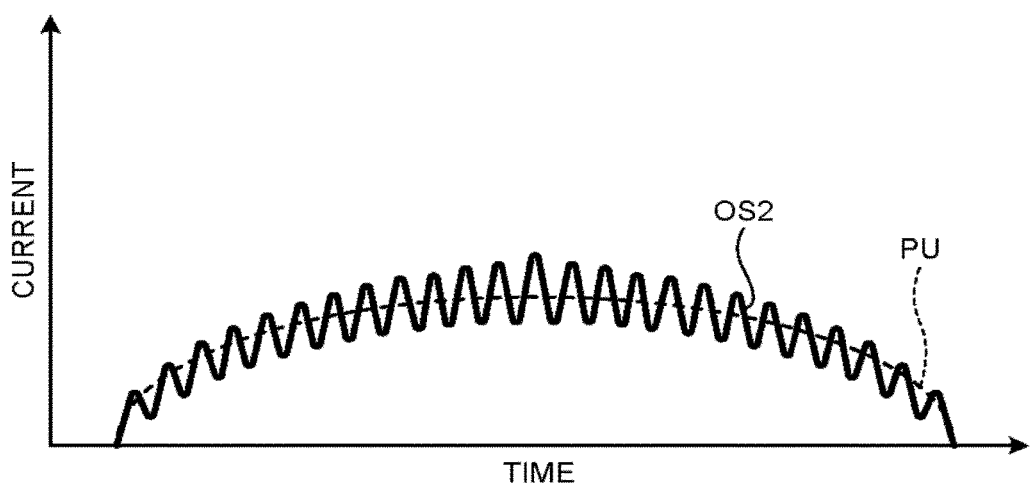
FIG. 6 is a graph illustrating an example of an oscillating component smoothed by a capacitor.
Figure 7:
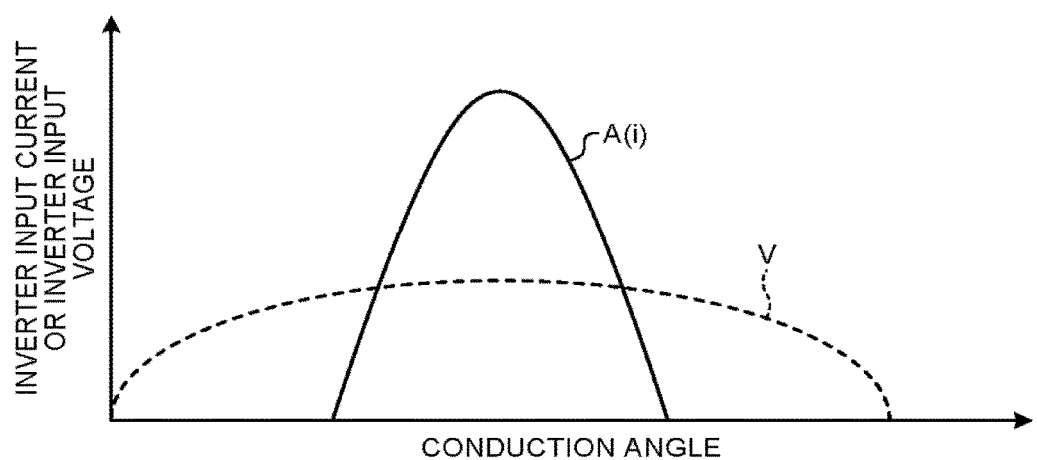
FIG. 7 is a graph illustrating an example of the case where a difference in conduction angle between an inverter input current and an inverter input voltage is large.
Figure 8:
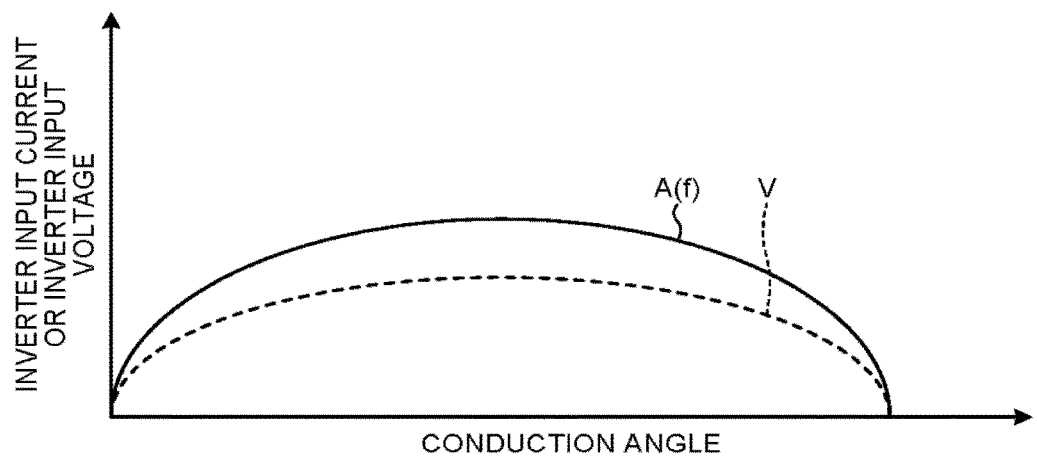
FIG. 8 is a graph illustrating an example of the case where the difference in conduction angle between the inverter input current and the inverter input voltage is small.
Figure 9:
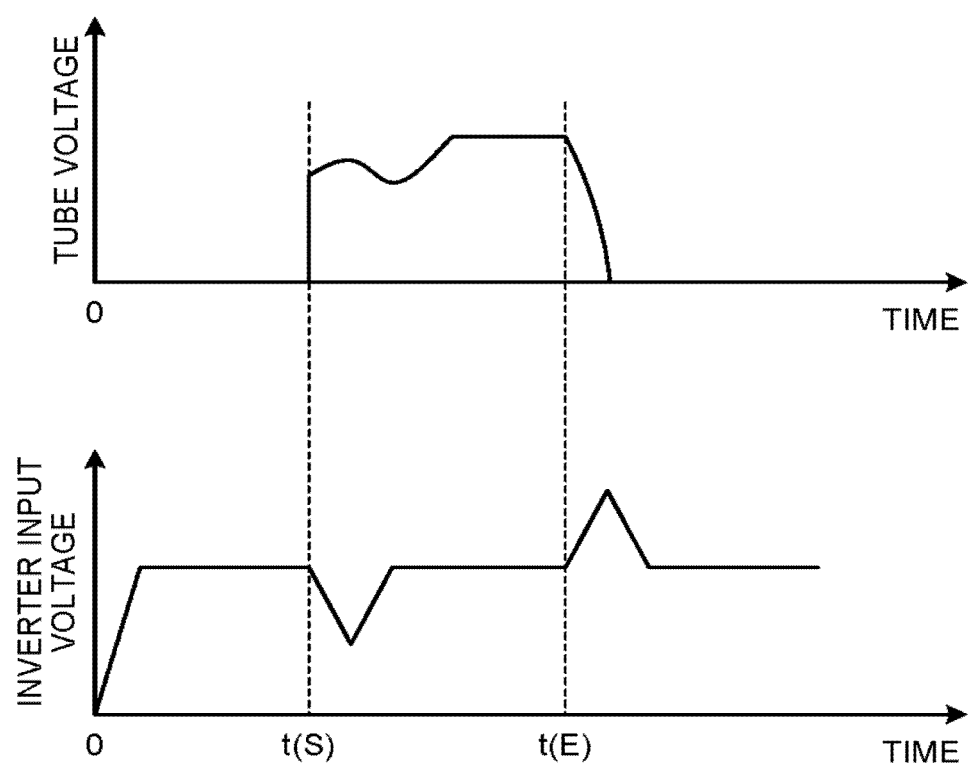
FIG. 9 is a graph illustrating temporal changes of the inverter input voltage and a tube voltage in the case where a gain is not switched.
Figure 10:
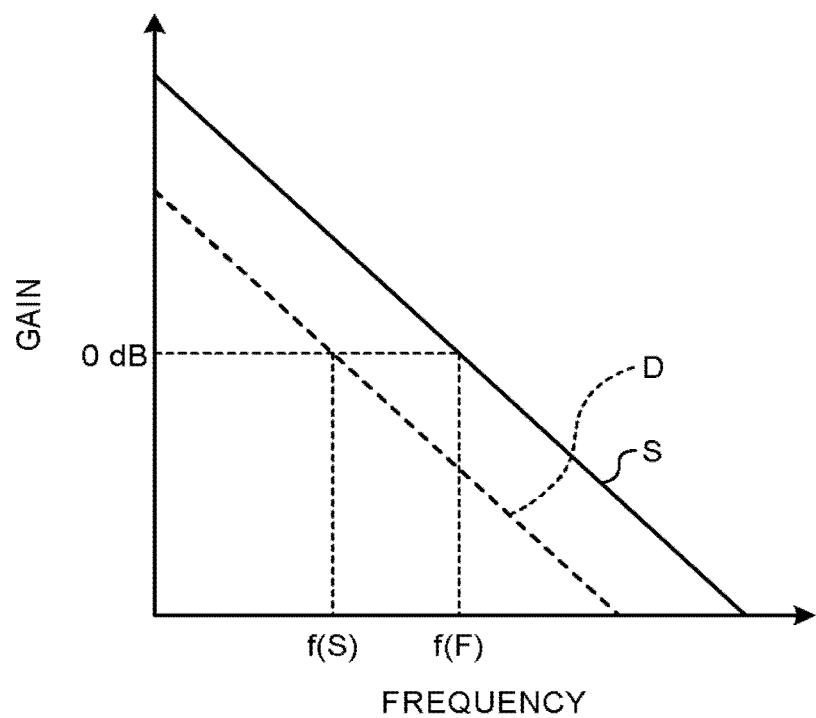
FIG. 10 is a graph illustrating frequency characteristics of a gain of the feedback circuitry.
Figure 11:
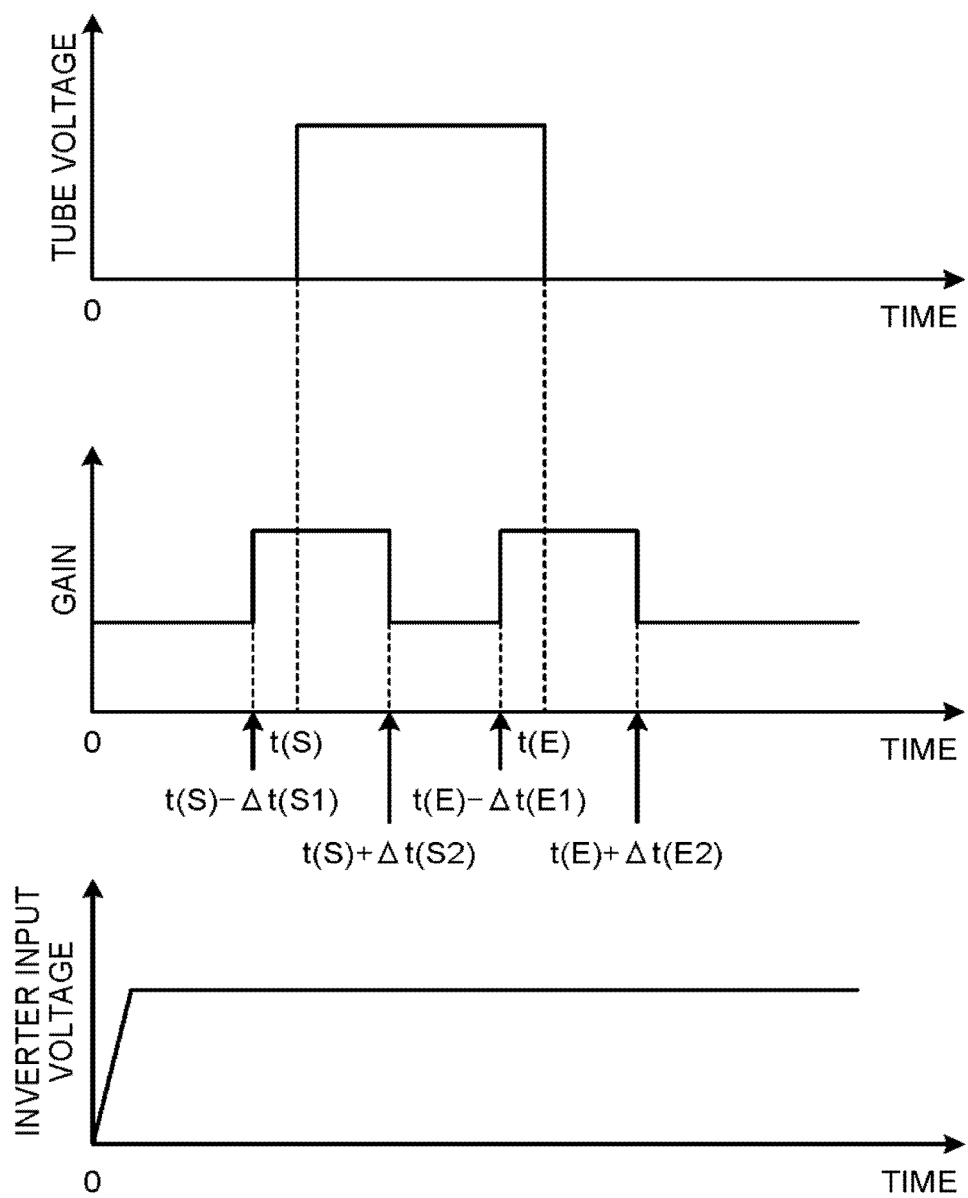
FIG. 11 is a graph illustrating temporal changes of the inverter input voltage, the tube voltage, and the gain in the case where the gain is switched.

Referring to FIG. 5 to FIG. 11, the operation of the high voltage generation apparatus 3 according to the first embodiment is now described. FIG. 5 is a graph illustrating an example of an oscillating component contained in a pulsating current generated by full-wave rectification. FIG. 6 is a graph illustrating an example of an oscillating component smoothed by a capacitor. FIG. 7 is a graph illustrating an example of the case where a difference in conduction angle between an inverter input current and an inverter input voltage is large. FIG. 8 is a graph illustrating an example of the case were the difference in conduction angle between the inverter input current and the inverter input voltage is small. FIG. 9 is a graph illustrating temporal changes of the inverter input voltage and a tube voltage in the case where a gain is not switched. FIG. 10 is a graph illustrating frequency characteristics of the gain of the feedback circuitry. FIG. 11 is a graph illustrating temporal changes of the inverter input voltage, the tube voltage, and the gain in the case where the gain is switched.

The AC power source 301 generates an alternating current. This alternating current is, for example, a sinusoidal alternating current. The diode 3021, the diode 3022, the diode 3023, and the diode 3024 have a rectifying action. Accordingly, the diode 3021, the diode 3022, the diode 3023, and the diode 3024 can rectify the alternating current generated by the AC power source 301. Specifically, the diode 3021, the diode 3022, the diode 3023, and the diode 3024 can full-wave rectify the alternating current generated by the AC power source 301.

In FIG. 3, when the alternating current generated by the AC power source 301 flows in the clockwise direction, the alternating current flows through the AC power source 301, the diode 3021, the capacitor 303, the diode 3022, and the AC power source 301 in this order. In FIG. 3, when the alternating current generated by the AC power source 301 flows in the counterclockwise direction, the alternating current flows through the AC power source 301, the diode 3023, the capacitor 303, the diode 3024, and the AC power source 301 in this order. Accordingly, the current flowing through the capacitor 303 flows from a terminal connected to the cathode of the diode 3021 and the cathode of the diode 3023 to a terminal connected to the anode of the diode 3022 and the anode of the diode 3024, irrespective of the flowing direction of the alternating current generated by the AC power source 301. Thus, the alternating current generated by the AC power source 301 becomes, for example, a pulsating current PU illustrated in FIG. 5 through the full-wave rectification.

The period of the pulsating current PU is half the period of the alternating current generated by the AC power source 301. For example, as illustrated in FIG. 5, the pulsating current PU contains an oscillating component OS1 whose period is shorter than the period of the pulsating current PU. The oscillating component OS1 is generated when the switching circuitry 309 switches the conductive state and non-conductive state of the n-type MOSFET 305 with a period shorter than the period of the pulsating current. Thus, the period of the oscillating component OS1 is equal to the period with which the switching circuitry 309 switches the conductive state and non-conductive state of the n-type MOSFET 305. Note that such an oscillating component is also called "ripple".

The capacitor 303 is charged when a large current flows, and is discharged when a small current flows. As illustrated in FIG. 5, the period of the oscillating component OS1 is greatly different from the period of the pulsating current PU. Thus, the oscillating component OS1 contained in the pulsating current PU illustrated in FIG. 5 can be smoothed. Then, the oscillating component OS1 illustrated in FIG. 5 becomes, for example, an oscillating component OS2 illustrated in FIG. 6. The amplitude of the oscillating component OS2 is smaller than the amplitude of the oscillating component OS1. Note that the capacitor 303 has capacitance of several µF, for example. The reason is that when the capacitance of the capacitor 303 is large, the waveform of the pulsating current PU is deformed and the power factor of the high voltage generation apparatus 3 cannot be improved. Such suppression in amplitude of the oscillating component is also called "critical mode control".

When the n-type MOSFET 305 is in the conductive state, the coil 304 stores energy therein by conducting the pulsating current whose oscillating component is smoothed by the capacitor 303. Then, when the n-type MOSFET 305 is in the non-conductive state, the coil 304 discharges the energy to the anode of the diode 306 as a direct current. The diode 306 conducts the direct current discharged from the coil 304, and supplies the direct current to the capacitor 307. Accordingly, electric charges are accumulated in the capacitor 307 to increase the voltage between two terminals of the capacitor 307.

The feedback circuitry 308 performs negative feedback control so that the voltage between two terminals of the capacitor 307 becomes a predetermined reference voltage. Specifically, when the voltage between two terminals of the capacitor 307 is equal to or higher than the reference voltage, the feedback circuitry 308 stops the operation of the switching circuitry 309 for increasing the voltage between two terminals of the capacitor 307. Specifically, in this case, the feedback circuitry 308 controls the switching circuitry 309 to stop the transmission of a signal for switching the conductive state and non-conductive state of the n-type MOSFET 305. When the voltage between two terminals of the capacitor 307 is lower than the reference voltage, the feedback circuitry 308 continues the operation of the switching circuitry 309 for increasing the voltage between two terminals of the capacitor 307. Specifically, in this case, the feedback circuitry 308 controls the switching circuitry 309 to continue the transmission of the signal for switching the conductive state and non-conductive state of the n-type MOSFET 305.

The switching circuitry 309 transmits the signal for switching the conductive state and non-conductive state of the n-type MOSFET 305 to the gate electrode of the n-type MOSFET 305 under control of the feedback circuitry 308. This signal is, for example, a rectangular wave with a frequency of from 30 kHz to 100 kHz. For example, the n-type MOSFET 305 becomes the conductive state when the rectangular wave is at High level, and becomes the non-conductive state when the rectangular wave is at Low level. The signal has a high frequency, and hence the high voltage generation apparatus 3 can downsize the capacitor 303 and the coil 304.

As illustrated in FIG. 7, when the difference in conduction angle between an inverter input current A(i) and an inverter input voltage V is large, the power factor of the high voltage generation apparatus 3 decreases. Accordingly, the apparent power, capacity, dimensions, and weight of the AC power source 301 increase.

To address with this, the frequency of negative feedback control by the feedback circuitry 306 is set to be lower than the frequency of the alternating current generated by the AC power source 301. For example, the frequency of negative feedback control by the feedback circuitry 308 is from 5 Hz to 10 Hz. As described above, the capacitor 303 smoothes the oscillating component contained in the pulsating current generated by full-wave rectification. Thus, the high voltage generation apparatus 3 improves the power factor by reducing the difference in conduction angle between an inverter input current A(f) and the inverter input voltage V as illustrated in FIG. 8. Consequently, the increase in apparent power, capacity, dimensions, and weight of the AC power source 301 is suppressed.

As described above, however, in the feedback circuitry 308, the frequency of negative feedback control is set to be lower than the frequency of the alternating current supplied from the AC power source 301. Thus, when a load applied to the high voltage generation apparatus 3 abruptly fluctuates due to the start or end of irradiation of X-rays by the X-ray tube 6, the control of the voltage between two terminals of the capacitor 307 by the feedback circuitry 308 is delayed.

For example, as Illustrated in the upper section in FIG. 9, when the X-ray tube 6 starts the irradiation of X-rays at the time t(S), the load applied to the high voltage generation apparatus 3 abruptly increases. Accordingly, as illustrated in the lower section in FIG. 9, the inverter input voltage temporarily decreases. Thus, as illustrated in the upper section in FIG. 9, the tube voltage supplied to the X-ray tube 6 fluctuates. As a result, for example, the dose of the X-rays radiated from the X-ray tube 6 fluctuates.

As illustrated in the upper section in FIG. 9, when the X-ray tube 6 ends the irradiation of X-rays at the time t(E), the load applied to the high voltage generation apparatus 3 abruptly decreases. Accordingly, as illustrated in the lower section in FIG. 9, the inverter input voltage temporarily increases. Thus, as illustrated in the upper section in FIG. 9, the high voltage generation apparatus 3 supplies the tube voltage to the X-ray tube 6 even after the time t(E). As a result, the X-ray tube 6 generates X-rays even in a period where the X-rays are not intended to be radiated. To address with this, the X-ray CT apparatus 1 performs the following control.

Frequency characteristics of the gain of the feedback circuitry 308 illustrated in FIG. 10 is now described. The resistance value of the first resistor 3083 is represented by R, and the impedance between the inverting input terminal and the output terminal of the operational amplifier 3086 is represented by Z. Then, the frequency characteristics of the gain of the feedback circuitry 308 are represented by Z/R.

When the switch 3084 is off, R is large and hence the frequency characteristics of the gain of the feedback circuitry 308 are indicated by, for example, the dotted line D illustrated in FIG. 10. In this case, the gain is small and the response speed of the feedback circuitry 308 is low. When a signal with a frequency f(S) is input to the feedback circuitry 308, the gain is 0 dB and hence the feedback circuitry 308 performs negative feedback control with the frequency f(S). When a signal with a frequency f(F) is input to the feedback circuitry 308, the gain is smaller than 0 dB and hence the feedback circuitry 308 performs negative feedback control with a frequency lower than the frequency f(F).

When the switch 3084 is on, R is small and hence the frequency characteristics of the gain of the feedback circuitry 308 are indicated by, for example, the solid line S illustrated in FIG. 10. In this case, the gain is large and the response speed of the feedback circuitry 308 is high. When the signal with the frequency f(S) is input to the feedback circuitry 308, the gain is larger than 0 dB and hence the feedback circuitry 308 performs negative feedback control with a frequency higher than the frequency f(S). When the signal with the frequency f(F) is input to the feedback circuitry 308, the gain is 0 dB and hence the feedback circuitry 308 performs negative feedback control with the frequency f(F).

The gain adjustment circuitry is included in the power factor improvement circuitry, and adjusts a gain of output power relative to reference power so that the gain differs between a first period including a rise of the output power or a fall of the output power and a second period different from the first period. Furthermore, the gain adjustment circuitry is included in a power supply apparatus included in the X-ray CT apparatus 1. For example, the gain adjustment circuitry is included in the power factor improvement circuitry, and adjusts a gain of an output voltage relative to a reference voltage so that the gain differs between a first period including the start of irradiation of X-rays by the X-ray tube 6 or the end of irradiation of X-rays by the X-ray tube 6 and a second period different from the first period. The second period includes a period between a plurality of the first periods at the time of the output from the X-ray tube 6. The gain adjustment circuitry adjusts the gain in accordance with frequency fluctuations at the time of the put from the X-ray tube 6.

Specifically, the switch operation mechanism 3085 operates as follows. The switch operation mechanism 3085 operates the switch when the voltage output from the power factor improvement circuitry fluctuates due to the start of irradiation of X-rays by the X-ray tube 6. For example, the switch operation mechanism 3085 continues to operate the switch for a predetermined period including the time point at which the X-ray tube 6 starts the irradiation of X-rays. Note that the following description takes as an example the case where, as illustrated in the upper section in FIG. 11, the load applied to the high voltage generation apparatus 3 abruptly increases from the time t(S) to the time t(S)+Δt(S2) illustrated in the middle section in FIG. 11 and the load applied to the high voltage generation apparatus 3 abruptly decreases from the time t(E) to the time t(E2) illustrated in the middle section in FIG. 11. Note that the time t(S) and the time t(E) are already known from, for example, a scan plan of the X-ray CT apparatus 1. The following contents can he applied to either of the case where the X-ray tube intermittently radiates X-rays and the case where the X-ray tube 6 continuously radiates X-rays.

The processing circuitry 46 uses the switch operation function 462 to transmit, at Step S1, a signal for switching ON and OFF of the switch 3084 to the switch operation mechanism 3085 at the time t(S)−Δt(S1) illustrated in the middle section in FIG. 11. The time t(S)−Δt(S1) is the time earlier by Δt(S1) than the time t(S) at which the high voltage generation apparatus 3 starts to supply the tube voltage to the X-ray tube 6. The switch operation mechanism 3085 receives the signal to turn on the switch 3084. Accordingly, the response speed of the feedback circuitry 308 is increased. Consequently, even when the load applied to the high voltage generation apparatus 3 abruptly increases due to the start of irradiation of X-rays by the X-ray tube 6, the high voltage generation apparatus 3 can maintain the inverter input voltage to a constant value as illustrated in the lower section in FIG. 11.

The processing circuitry 46 transmits, at Step S1, the signal for switching ON and OFF of the switch 3084 to the switch operation mechanism 3085 at the time t(S)+Δt(S2) illustrated in the middle section in FIG. 11. The time t(S)+Δt(S2) is the time later by Δt(S2) than the time t(S) at which the high voltage generation apparatus 3 starts to supply the tube voltage to the X-ray tube 6. The switch operation mechanism 3085 receives the signal to turn off the switch 3084. Accordingly, the response speed of the feedback circuitry 308 is decreased. Consequently, the high voltage generation apparatus 3 can maintain a high power factor while the X-ray tube continues the irradiation of X-rays.

The switch operation mechanism 3085 operates the switch when the voltage output from the power factor improvement circuitry fluctuates due to the end of irradiation of X-rays by the X-ray tube 6. For example, the switch operation mechanism 3085 continues to operate the switch for a predetermined period including the time point at which the X-ray tube 6 ends the irradiation of X-rays.

The processing circuitry 46 transmits, at Step S1, the signal for switching ON and OFF of the switch 3084 to the switch operation mechanism 3085 at the time t(E)−Δt(E1) illustrated in the middle section in FIG. 11. The time t(E)−Δt(E1) is the time earlier by Δt(E1) than the time t(E) at which the high voltage generation apparatus 3 starts to upply the tube voltage to the X-ray tube 6. The switch operation mechanism 3085 receives the signal to turn on the switch 3084. Accordingly, the response speed of the feedback circuitry 308 is increased. Consequently, even when the load applied to the high voltage generation apparatus 3 abruptly decreases due to the end of irradiation of X-rays by the X-ray tube 6, the high voltage generation apparatus 3 can maintain the inverter input voltage to a constant value as illustrated in the lower section in FIG. 11.

The processing circuitry 46 transmits, at Step S1, the signal for switching ON and OFF of the switch 3084 to the switch operation mechanism 3065 at the time t(E)+Δt(E2) illustrated in the middle section in FIG. 11. The time t(E)+Δt(E2) is the time later by Δt(E2) than the time t(E) at which the high voltage generation apparatus 3 starts to supply the tube voltage to the X-ray tube 6. The switch operation mechanism 3085 receives the signal to turn off the switch 3084. Accordingly, the response speed of the feedback circuitry 308 is decreased. Consequently, the high voltage generation apparatus 3 can maintain a high power factor even after the end of irradiation of X-rays by the X-ray tube 6.

The inverter circuitry 310 converts a direct current supplied from the power factor improvement circuitry into an alternating current. The inverter circuitry 310 adjusts the voltage output to the high voltage generation circuitry 311 through negative feedback control performed by the feedback circuitry 312. In this manner, the high voltage generation apparatus 3 adjusts the tube voltage supplied to the X-ray tube 6.

The feedback circuitry 312 performs negative feedback control so that the tube voltage supplied from the high voltage generation circuitry 311 to the X-ray tube 6 becomes a desired voltage. Specifically, when the tube voltage pplied from the high voltage generation circuitry 311 to the X-ray tube 6 is equal to or higher than a reference voltage, the feedback circuitry 312 stops the operation of increasing the tube voltage. Specifically, in this case, the feedback circuitry 312 controls the switching circuitry 313 to stop the transmission of a signal for switching the conductive state and non-conductive state of the switching elements.

When the tube voltage supplied from the high voltage generation circuitry 311 to the X-ray tube 6 is lower than the reference voltage, the feedback circuitry 312 continues the operation of the switching circuitry 313 for increasing the tube voltage between two terminals of the capacitor 307. Specifically, in this case, the feedback circuitry 312 controls the switching circuitry 313 to continue the transmission of the signal for switching the conductive state and non-conductive state of the switching elements.

The switching circuitry 313 controls the switching elements included in the inverter circuitry 310 by, for example, pulse width modulation (PWM) control, thereby controlling the tube voltage supplied from the high voltage generation circuitry 311 to the X-ray tube 6.

As described above, the high voltage generation apparatus 3 according to the first embodiment operates the switch 3084 with the switch operation mechanism 3085 when the voltage output from the power factor improvement rcuitry fluctuates due to at least one of the start of irradiation of X-rays by the X-ray tube 6 or the end of irradiation of X-rays by the X-ray tube 6, thereby increasing the response speed of the feedback circuitry 308. Consequently, the high voltage generation apparatus 3 can maintain the inverter input voltage to a constant value even when the load abruptly increases due to the start of irradiation of X-rays by the X-ray tube 6 or even when the load abruptly decreases due to the end of irradiation of X-rays by the X-ray tube 6.

Note that the power factor of the high voltage generation apparatus 3 decreases when the response speed of the feedback circuitry 308 is increased. The decrease in power factor, however, can be suppressed by an input filter connected to both terminals of the AC power source 301. Specifically, the decrease in power factor can be suppressed by a parasitic normal component in a line filter or an X capacitor.

The period during which the voltage output from the power factor improvement circuitry fluctuates due to the start of irradiation of X-rays by the X-ray tube 6 or the end of irradiation of X-rays by the X-ray tube 6 is much shorter than the period during which the X-ray tube 6 radiates X-rays. Consequently, the high voltage generation apparatus 3 can maintain a high power factor.

The high voltage generation apparatus 3 needs no reactor. Consequently, the high voltage generation apparatus 3 can reduce apparent power of the AC power source 301 configured to supply power to the X-ray tube 6 to suppress the capacity of the AC power source 301 while suppressing the increase in dimensions and weight of the high voltage generation apparatus 3. As a result, a line filter, an X capacitor, and a fuse installed between the AC power source 301 and the X capacitor can be downsized.

The high voltage generation apparatus 3 adjusts the voltage output from the inverter circuitry 310 to the high voltage generation circuitry 311, thereby adjusting the tube voltage supplied to the X-ray tube 6. Consequently, the high voltage generation apparatus 3 can exhibit the above-mentioned effects without changing its configuration.

Second Embodiment

A high voltage generation apparatus 3a according to a second embodiment is now described. The same components as those in the first embodiment are denoted by the same reference symbols as those in the description of the first embodiment. Note that detailed descriptions of the contents overlapping with those in the first embodiment are omitted.

Figure 12:
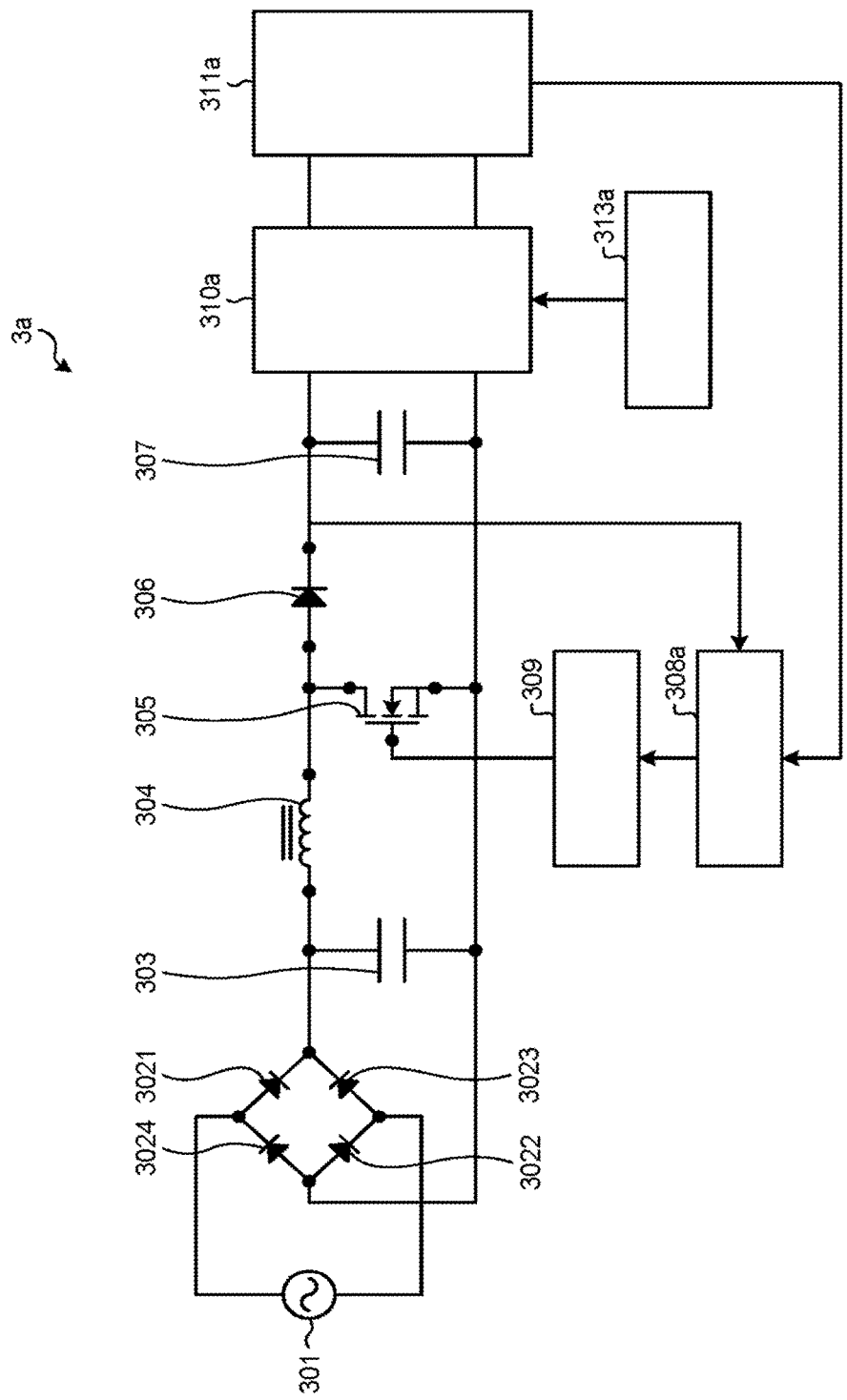
FIG. 12 is a diagram illustrating a configuration example of a high voltage generation apparatus according to a second embodiment.

Referring to FIG. 12, the configuration of the high voltage generation apparatus 3a according to the second embodiment is now described. FIG. 12 is a diagram illustrating a configuration example of the high voltage generation apparatus according to the second embodiment. The high voltage generation apparatus 3 according to the first embodiment adjusts a tube voltage by adjusting an output voltage of the inverter circuitry 310. The high voltage generation apparatus 3a according to the second embodiment adjusts a tube voltage by adjusting an inverter input voltage.

As illustrated in FIG. 12, the high voltage generation apparatus 3a includes an AC power source 301, a diode 3021, a diode 3022, a diode 3023, a diode 3024, a capacitor 303, coil 304, an n-type MOSFET 305, a diode 306, a capacitor 307, feedback circuitry 308a, switching circuitry 309, inverter circuitry 310a, high voltage generation circuitry 311a, and switching circuitry 313a.

The configuration of the feedback circuitry 308a is the same as that of the feedback circuitry 308 according to the first embodiment. A first input terminal of the feedback circuitry 308a is connected to a cathode of the diode 306 and one terminal of the capacitor 307. A second input terminal of the feedback circuitry 308a is connected to the high voltage generation circuitry 311a. The second input terminal of the feedback circuitry 308a supplies a non-inverting input terminal of an operational amplifier with a voltage obtained by dividing a tube voltage supplied from the high voltage generation circuitry 311a to the X-ray tube 6 by a boosting ratio n.

The boosting ratio n is a value obtained by dividing the tube voltage supplied from the high voltage generation circuitry 811a to the X-ray tube 6 by an inverter input voltage. As described above, the coil 304, the n-type MOSFET 305, the diode 306, and the capacitor 307 form booster circuitry. Accordingly, the high voltage generation apparatus 3a cannot decrease the inverter input voltage to be smaller than the AC voltage supplied from the AC power source 301.

Thus, when the AC power source 301 supplies a single-phase alternating current, the boosting ratio n needs to be set so that the inverter input voltage is higher than the square root of 2 times the voltage of the single-phase alternating current in the entire range of the tube voltage. When the AC power source 301 supplies a three-phase alternating current, the boosting ratio n needs to be set so that the inverter input voltage is higher than the square root of 3 times the voltage of the three-phase alternating current in the entire range of the tube voltage.

The switching circuitry 313a is connected to switching elements included in the inverter circuitry 310a.

The operation of the high voltage generation apparatus 3a according to the second embodiment is now described. The feedback circuitry 308a performs negative feedback control so that the voltage between two terminals of the capacitor 307 becomes a voltage obtained by dividing the tube voltage supplied from the high voltage generation circuitry 311a to the X-ray tube 6 by the boosting ratio n. Specifically, when the voltage between two terminals of the capacitor 307 is equal to or higher than the voltage obtained by dividing the tube voltage supplied from the high voltage generation circuitry 311a to the X-ray tube 6 by the boosting ratio n, the feedback circuitry 308a stops the operation of the switching circuitry 309 for increasing the voltage between two terminals of the capacitor 307. Specifically, in this case, the feedback circuitry 308a controls the switching circuitry 309 to stop the transmission of a signal for switching the conductive state and non-conductive state of the n-type MOSFET 305.

When the voltage between tarn terminals of the capacitor 307 is lower than the voltage obtained by dividing the tube voltage supplied from the high voltage generation circuitry 311a to the X-ray tube 6 by the boosting ratio n, the feedback circuitry 308a continues the operation of the switching circuitry 309 for increasing the voltage between two terminals of the capacitor 307. Specifically, in this case, the feedback circuitry 308a controls the switching circuitry 309 to continue the transmission of the signal for switching the conductive state and non-conductive state of the n-type MOSFET 305.

The switching circuitry 313a transmits the signal for switching the conductive state and the non-conductive state to the switching elements included in the inverter circuitry 310a. The duty ratio of the signal is 50%. In this manner, the switching circuitry 313a controls the inverter circuitry 310a so that the inverter circuitry 310a continues to supply the voltage to the high voltage generation circuitry 311a except for a dead time. Thus, the above-mentioned boosting ratio n has a constant value.

As described above, the high voltage generation apparatus 3a according to the second embodiment operates the switch 3084 with the switch operation mechanism 3085 when the voltage output from the power factor improvement circuitry fluctuates due to at least one of the start of irradiation of X-rays by the X-ray tube 6 or the end of irradiation of X-rays by the X-ray tube 6, thereby increasing the response speed of the feedback circuitry 308a. Consequently, the high voltage generation apparatus 3a can maintain the inverter input voltage to a constant value even when the load abruptly increases due to the start of irradiation of X-rays by the X-ray tube 6 or even when the load abruptly decreases due to the end of irradiation of X-rays by the X-ray tube 6.

Note that the power factor of the high voltage generation apparatus 3a decreases when the response speed the feedback circuitry 308a is increased. However, the decrease in power factor can be suppressed by an input filter connected to both terminals of the AC power source 301. Specifically, the decrease in power factor can be suppressed by a parasitic normal component in a line filter or an X capacitor.

The period during which the voltage output from the power factor improvement circuitry fluctuates due to the start of irradiation of X-rays by the X-ray tube 6 or the end of irradiation of X-rays by the X-ray tube 6 is much shorter than the period during which the X-ray tube 6 radiate X-rays. Consequently, the high voltage generation apparatus 3a can maintain a high power factor.

The high voltage generation apparatus 3a needs no reactor. Consequently, the high voltage generation apparatus 3a can reduce apparent power of the AC power source 301 configured to supply power to the X-ray tube 6 to suppress the capacity of the AC power source 301 while suppressing the increase in dimensions and weight of the high voltage generation apparatus 3a. As a result, a line filter, an X capacitor, and a fuse installed between the AC power source 301 and the X capacitor can be downsized.

The high voltage generation apparatus 3a adjusts the inverter input voltage, thereby adjusting the tube voltage supplied to the X-ray tube 6. Consequently, the high voltage generation apparatus 3a can avoid the occurrence of switching loss caused by pulse width modulation control performed by the high voltage generation apparatus 3 according to the first embodiment. Unlike the high voltage generation apparatus 3 according to the first embodiment, the high voltage generation apparatus 3a can omit feedback circuitry configured to control the switching circuitry 313a.

The high voltage generation apparatus 3 according to the first embodiment or the high voltage generation apparatus according to the second embodiment may not include the diode 3023 and the diode 3024. In this case, the diode 3021 and the diode 3022 half-wave rectify the alternating current generated by the AC power source 301. Accordingly, the alternating current generated by the AC power source 301 is a pulsating current obtained by half-wave rectification.

The high voltage generation apparatus 3 or the high voltage generation apparatus 3a may include an insulated gate bipolar transistor (IGBT) instead of the n-type MOSFET 305.

In the first embodiment and the second embodiment, the switch 3084 changes the resistance value of the first resistor 3083, but the embodiments are not limited thereto. The switch included in the high voltage generation apparatus 3 or the high voltage generation apparatus 3a is configured to perform at least one of the following: change the resistance value of the first resistor 3083; charge the resistance value of the second resistor 3087; or change the capacitance of at least one of the capacitor 3088 or the capacitor 3089 within the range where negative feedback is applied to the operational amplifier 3086.

The switch discretely changes at least ore of the resistance value of the first resistor 3083, the resistance value of the second resistor 3087, or the capacitance of at least one of the capacitor 3088 or the capacitor 3089. The switch may continuously change at least one of the resistance value of the first resistor 3083, the resistance value of the second resistor 3087, or the capacitance of at least one of the capacitor 3088 or the capacitor 3089.

Note that it is preferred that the switch change at least one of the resistance value of the first resistor 3083 or the resistance value of the second resistor 3087 rather than changing the capacitance of at least one of the capacitor 3088 or the capacitor 3089. The reason is that when the capacitance of at least one of the capacitor 3088 or the capacitor 3089 is changed, positive feedback may be applied to the operational amplifier 3086 so that the feedback circuitry 308 or the feedback circuitry 308*a* oscillates.

The second resistor 3087 may include a plurality of resistors similarly to the first resistor 3083. The number of resistors included in the second resistor 3087 is not particularly limited. In this case, the feedback circuitry 308 or the feedback circuitry 308*a* includes a switch configured to switch a resistor that contributes to the resistance value of the second resistor 3087 among the resistors, and a switch operation mechanism configured to operate the switch. The switch operation mechanism is an example of gain adjustment circuitry. The gain adjustment circuitry switches the switch to switch the resistance value of the second resistor 3087 so that the gain is increased for the first period.

At least one of the first resistor 3083 or the second resistor 3087 may be a variable resistor. In this case, at least one of the feedback circuitry 308 or the feedback circuitry 308*a* includes a switch configured to change a resistance value of the variable resistor and a switch operation mechanism configured to operate the switch.

Note that it is preferred that at least one of the first resistor 3083 or the second resistor 3087 include a plurality of resistors rather than being a variable resistor. The reason is that the cost of a plurality of resistors, a switch, and a switch operation mechanism configured to operate the switch is lower than the cost of a variable resistor in many cases. Another reason is that when at least one of the first resistor 3083 or the second resistor 3087 includes a plurality of resistors, the high voltage generation apparatus 3 or the high voltage generation apparatus 3*a* can instantaneously switch a resistance value optimum for maintaining the inverter input voltage to a constant value and a resistance value optimum for improving the power factor.

The capacitor included in the feedback circuitry 308 or the feedback circuitry 308*a* may include a plurality of sub-capacitors. The number of sub-capacitors included in the capacitor of the feedback circuitry 308 or the feedback circuitry 308*a* is not particularly limited. In this case, the feedback circuitry 308 or the feedback circuitry 308*a* includes a switch configured to switch a sub-capacitor that contributes to the capacitance of the capacitor included in the feedback circuitry 308 or the feedback circuitry 308*a* among the sub-capacitors, and a switch operation mechanism configured to operate the switch. The switch operation mechanism is an example of gain adjustment circuitry. The gain adjustment circuitry switches the switch to switch the capacitance of the capacitor so that the gain is increased for the first period. The switch operation mechanism needs to change the capacitance of the capacitor within the range where negative feedback is applied to the operational amplifier 3086. The reason is that when positive feedback is applied to the operational amplifier 3086, the feedback circuitry 308 or the feedback circuitry 308*a* oscillates.

Figure 13:
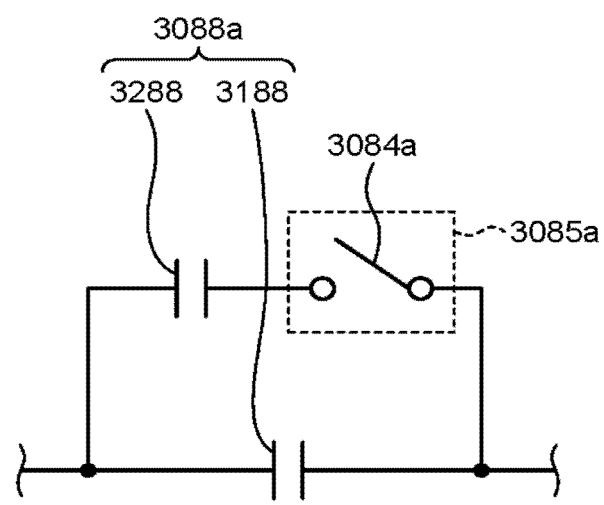
FIG. 13 is a diagram illustrating an example of a capacitor, a switch, and a switch operation mechanism included in the feedback circuitry.

The feedback circuitry 308 or the feedback circuitry 308*a* may include, for example, a capacitor 3088*a*, a switch 3084*a*, and a switch operation mechanism 3085*a* illustrated in FIG. 13 instead of the capacitor 3088. As illustrated in FIG. 13, the capacitor 3088*a* includes a sub-capacitor 3188 and a sub-capacitor 3288. Furthermore, the feedback circuitry 308 or the feedback circuitry 308*a* may include the capacitor 3088*a*, the switch 3084*a*, and the switch operation mechanism 3085*a* illustrated in FIG. 13 instead of the capacitor 3089.

The capacitor included in at least one of the feedback circuitry 308 or the feedback circuitry 308*a* may be a variable capacitor. In this case, at least one of the feedback circuitry 308 or the feedback circuitry 308*a* includes a switch configured to change the capacitance value of the variable capacitor and a switch operation mechanism configured to operate the switch.

Note that it is preferred that the capacitor included in the feedback circuitry 308 or the feedback circuitry 308*a* includes a plurality of sub-capacitors rather than being a variable capacitor. The reason is that the cost of a plurality of sub-capacitors, a switch, and a switch operation mechanism configured to operate the switch is lower than the cost of a variable capacitor in many cases. Another reason is that when the capacitor included in the feedback circuitry 308 or the feedback circuitry 308*a* includes a plurality of sub-capacitors, the high voltage generation apparatus 3 or the high voltage generation apparatus 3*a* can instantaneously switch the capacitance optimum for maintaining the inverter input voltage to a constant value and the capacitance optimum for improving the power factor.

The configuration of the feedback circuitry 308 and the feedback circuitry 308*a* is not limited to the configuration illustrated in FIG. 4. In the feedback circuitry 308 and the feedback circuitry 308*a*, it is sufficient that a capacitor and a resistor are provided between the inverting input terminal and the output terminal of the operational amplifier 3086.

In the first embodiment and second embodiment, the switch operation mechanism 3085 operates the switch before the voltage output from the power factor improvement circuitry fluctuates, but the embodiments are not limited thereto. For example, the switch operation mechanism 3085 may operate the switch 3084 at the same time as the occurrence of fluctuations in voltage output from the power factor improvement circuitry. For another example, the switch operation mechanism 3085 may operate the switch 3084 after the voltage output from the power factor improvement circuitry fluctuates. In particular, the switch 3084 is often operated in these timings in the case where X-rays are manually radiated from the X-ray tube 6. In any case, the high voltage generation apparatus 3 and the high voltage generation apparatus 3*a* can exhibit the above-mentioned effects.

It is preferred that the response speed of the feedback circuitry 308 or the feedback circuitry 308*a* be switched when the fluctuations in load applied to the high voltage generation apparatus 3 or the high voltage generation apparatus 3*a* are large. The reason is that the power factor of the high voltage generation apparatus 3 or the high voltage generation apparatus 3*a* decreases when the response speed of the feedback circuitry 308 or the feedback circuitry 308*a* is increased as described above. Examples of the case where the fluctuations in load applied to the high voltage generation apparatus 3 or the high voltage generation apparatus 3*a* are large include when the X-ray tube 6 starts the irradiation of X-rays and when the X-ray tube 6 ends the irradiation of X-rays. Examples of the case where the fluctuations in load applied to the high voltage generation apparatus 3 or the high voltage generation apparatus 3*a* are small include when the X-ray tube 6 is radiating X-rays, when the X-ray tube 6 is not radiating X-rays, and when the X-ray tube 6 is modulating a tube current.

In the first embodiment and the second embodiment, the case where the high voltage generation apparatus 3 and the high voltage generation apparatus 3*a* are included in the X-ray CT apparatus 1 is exemplified, but the embodiments are not limited thereto. The high voltage generation apparatus 3 and the high voltage generation apparatus 3*a* may be included in a radiation diagnostic apparatus. The radiation diagnostic apparatus generates a medical image by using radiation. Examples of the radiation as used here include X-rays, γ-rays, electron beams, and proton beams. The high voltage generation apparatus 3 and the high voltage generation apparatus 3a supply an output voltage to an apparatus configured to generate radiation for generating a medical image. In these cases, the output voltage of the high voltage generation apparatus 3 or the high voltage generation apparatus 3a rises in response to the start of irradiation of radiation and falls in response to the end of irradiation of radiation. Power is the product of voltage and current. Accordingly, in these cases, the gain adjustment circuitry adjusts the gain of the output voltage relative to the reference voltage so that the gain differs between the first period and the second period. Consequently, the gain adjustment circuitry can adjust the gain of the output voltage relative to the reference voltage so that the gain differs between the first period and the second period.

For another example, the high voltage generation apparatus 3 and the high voltage generation apparatus 3a may be included in a linear accelerator (LINAC). The linear accelerator generates radiation for lesion treatment. Examples of the radiation as used here include X-rays, γ-rays, electron beams, and proton beams. The linear accelerator may be included in a radiation diagnostic apparatus. The high voltage generation apparatus 3 and the high voltage generation apparatus 3a supply an output voltage to the linear accelerator. In these cases, the output voltage of the high voltage generation apparatus 3 or the high voltage generation apparatus 3a rises in response to the start of irradiation of radiation and falls in response to the end of irradiation of radiation. Power is the product of voltage and current. Accordingly, in these cases, the gain adjustment circuitry adjusts the gain of the output voltage relative to the reference voltage so that the gain differs between the first period and the second period. Consequently, the gain adjustment circuitry can adjust the gain of the output voltage relative to the reference voltage so that the gain differs between the first period and the second period.

The power supply apparatus including the above-mentioned gain adjustment circuitry may supply a current to a shock wave generator included in an extracorporeal shock wave lithotripsy (ESWL) apparatus. For another example, the power supply apparatus including the above-mentioned gain adjustment circuitry may supply a current to a gradient amplifier included in a magnetic resonance imaging (MRI) apparatus. For another example, the power supply apparatus including the above-mentioned gain adjustment circuitry may supply a current to a medical laser apparatus. Examples of the medical laser apparatus include an apparatus for lesion treatment using a laser. In these cases, an output current of the power supply apparatus including the above-mentioned gain adjustment circuitry rises in response to the start of supply of current to the above-mentioned apparatus and falls in response to the end of supply of current to the above-mentioned apparatus. Power is the product of voltage and current. Accordingly, in these cases, the gain adjustment circuitry adjusts the gain of the output current relative to the reference current so that the gain differs between the first period and the second period. Consequently, the gain adjutment circuitry can adjust the gain of the output current relative to the reference current so that the gain differs between the first period and the second period.

Examples of the above-mentioned processor include a central processing unit (CPU), a graphics processing unit (GPU), an application specific integrated circuit (ASIC), a programmable logic device (PLD), and a field programmable gate array (FPGA). Examples of the programmable logic device (PLD) include a simple programmable logic device (SPLD) and a complex programmable logic device (CPLD).

In the above-mentioned embodiments, the high voltage generation apparatus 3, the collimator adjustment circuitry 4, the gantry drive circuitry 5, the data collection circuitry 10, the couch drive circuitry 22, and the processing circuitry 46 implement their functions by reading and executing the computer programs stored in the storage circuitry 45, but the embodiments are not limited thereto. Instead of storing the computer programs in the storage circuitry 45, the computer program may be directly embedded in each circuitry. In this case, each circuitry implements its function by reading and executing the computer program that is directly embedded therein.

The circuitry illustrated in FIG. 1 may be dispersed or integrated as appropriate. For example, the processing circuitry 46 may be dispersed in scan control circuitry, pre-processing circuitry, image generation circuitry, display control circuitry, and control circuitry that execute the scan control function 461, the pre-processing function 463, the image generation function 464, the display control function 465, and the control function 466, respectively. Furthermore, for example, the high voltage generation apparatus 3, the collimator adjustment circuitry 4, the gantry drive circuitry 5, the data collection circuitry 10, the couch drive circuitry 22, and the processing circuitry 46 may be integrated as appropriate.

According to at least one of the embodiments scribed above, the high voltage generation apparatus, the X-ray CT apparatus, and the power supply apparatus capable of improving the responsiveness to load fluctuations while improving the power factor can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A high voltage generation apparatus, comprising:
power factor improvement circuitry configured to improve a power factor of alternating current (AC) power output from an AC power source in order to supply an X-ray tube with power that is controlled based on a reference voltage; and
gain adjustment circuitry included in the power factor improvement circuitry, the gain adjustment circuitry being configured to adjust a gain of the AC power output from the AC power source relative to the reference voltage so that the gain differs between a first period including a start of irradiation of X-rays by the X-ray tube and an end of irradiation of X-rays by the X-ray tube, and a second period different from the first period.

2. The high voltage generation apparatus according to claim 1, wherein the gain adjustment circuitry is configured to adjust the gain in accordance with frequency fluctuations at a time of output from the X-ray tube.

3. The high voltage generation apparatus according to claim 1, wherein the second period comprises a period between a plurality of the first periods at a time of output from the X-ray tube.

4. The high voltage generation apparatus according to claim 2, further comprising:
an operational amplifier;
a first resistor that is connected to an inverting input terminal of the operational amplifier and to which a voltage output from the power factor improvement circuitry is input; and
a switch configured to change a resistance value of the first resistor, wherein
the gain adjustment circuitry is configured to switch the switch to switch the resistance value of the first resistor so that the gain is increased for the first period.

5. The high voltage generation apparatus according to claim 2, further comprising:
an operational amplifier;
a second resistor connected to an inverting input terminal of the operational amplifier and an output terminal of the operational amplifier; and
a switch configured to change a resistance value of the second resistor, wherein
the gain adjustment circuitry is configured to switch the switch to switch the resistance value of the second resistor so that the gain is increased for the first period.

6. The high voltage generation apparatus according to claim 2, further comprising:
an operational amplifier;
a capacitor connected to an inverting input terminal of the operational amplifier and an output terminal of the operational amplifier; and
a switch configured to change capacitance of the capacitor, wherein
the gain adjustment circuitry is configured to switch the switch to change the capacitance of the capacitor within a range where negative feedback is applied to the operational amplifier so that the gain is increased for the first period.

7. The high voltage generation apparatus according to claim 4, wherein the switch is configured to discretely change the resistance value of the first resistor.

8. The high voltage generation apparatus according to claim 4, wherein
the first resistor includes a plurality of resistors, and
the switch is configured to switch the resistor that contributes to the resistance value of the first resistor.

9. The high voltage generation apparatus according to claim 4, wherein the first resistor comprises a variable resistor.

10. The high voltage generation apparatus according to claim 5, wherein the switch is configured to discretely change the resistance value of the second resistor.

11. The high voltage generation apparatus according to claim 5, wherein
the second resistor includes a plurality of resistors, and
the switch is configured to switch the resistor that contributes to the resistance value of the second resistor.

12. The high voltage generation apparatus according to claim 5, wherein the second resistor comprises a variable resistor.

13. The high voltage generation apparatus according to claim 6, wherein
the capacitor includes a plurality of sub-capacitors, and
the switch is configured to switch the sub-capacitor that contributes to the capacitance of the capacitor.

14. The high voltage generation apparatus according to claim 6, wherein the capacitor comprises a variable capacitor.

15. The high voltage generation apparatus according to claim 4, wherein a predetermined voltage is input to a non-inverting input terminal of the operational amplifier.

16. The high voltage generation apparatus according to claim 4, wherein a voltage supplied to the X-ray tube is input to a non-inverting input terminal of the operational amplifier.

17. An X-ray computed tomography (CT) apparatus, comprising:
power factor improvement circuitry configured to improve a power factor of alternating current (AC) power output from an AC power source in order to supply an X-ray tube with power that is controlled based on a reference voltage; and
gain adjustment circuitry included in the power factor improvement circuitry, the gain adjustment circuitry being configured to adjust a gain of the AC power output from the AC power source relative to the reference voltage so that the gain differs between a first period including a start of irradiation of X-rays by the X-ray tube and an end of irradiation of X-rays by the X-ray tube, and a second period different from the first period.

18. A power supply apparatus, comprising:
power factor improvement circuitry configured to improve a power factor of alternating current (AC) power output from an AC power source in order to supply an X-ray tube with power that is controlled based on a reference voltage; and
gain adjustment circuitry included in the power factor improvement circuitry, the gain adjustment circuitry being configured to adjust a gain of the AC power output from the AC power source relative to reference power so that the gain differs between a first period including a rise of output power and a fall of the output power, and a second period different from the first period.

19. The power supply apparatus according to claim 18, wherein the gain adjustment circuitry is configured to adjust a gain of an output voltage relative to the reference voltage so that the gain differs between the first period and the second period.

20. The power supply apparatus according to claim 18, wherein the gain adjustment circuitry is configured to adjust a gain of an output current relative to a reference current so that the gain differs between the first period and the second period.

* * * * *